US010912820B2

(12) United States Patent
Schmetzer

(10) Patent No.: US 10,912,820 B2
(45) Date of Patent: Feb. 9, 2021

(54) USE OF IMMUNOMODULATORY KITS FOR IMMUNOTHERAPEUTIC TREATMENT OF PATIENTS WITH MYELOID LEUKEMIAS

(71) Applicant: Modiblast Pharma GmbH, Oberhaching (DE)

(72) Inventor: Helga Schmetzer, Oberhaching (DE)

(73) Assignee: Modiblast Pharma GmbH, Oberhaching (DE)

(*) Notice: Subject to any disclaimer, the term of this patent is extended or adjusted under 35 U.S.C. 154(b) by 153 days.

(21) Appl. No.: 15/956,343

(22) Filed: Apr. 18, 2018

(65) Prior Publication Data

US 2018/0303905 A1  Oct. 25, 2018

Related U.S. Application Data

(63) Continuation of application No. 15/517,627, filed as application No. PCT/EP2015/001979 on Oct. 8, 2015, now abandoned.

(30) Foreign Application Priority Data

Oct. 9, 2014 (DE) .................. 10 2014 014 993

(51) Int. Cl.
| | |
|---|---|
| *A61K 31/5575* | (2006.01) |
| *A61K 38/19* | (2006.01) |
| *A61K 39/09* | (2006.01) |
| *C07K 14/315* | (2006.01) |
| *C07K 14/535* | (2006.01) |
| *A61K 31/423* | (2006.01) |
| *A61K 31/43* | (2006.01) |
| *G01N 33/50* | (2006.01) |

(52) U.S. Cl.
CPC .......... *A61K 38/193* (2013.01); *A61K 31/423* (2013.01); *A61K 31/43* (2013.01); *A61K 31/5575* (2013.01); *A61K 38/191* (2013.01); *A61K 39/092* (2013.01); *C07K 14/315* (2013.01); *C07K 14/535* (2013.01); *G01N 33/505* (2013.01); *G01N 33/5011* (2013.01); *G01N 2800/52* (2013.01)

(58) Field of Classification Search
CPC .... A61K 38/18; A61K 38/193; A61K 31/557; A61K 31/5575; A61K 39/092; C07K 14/475; C07K 14/535; C07K 14/315
See application file for complete search history.

(56) References Cited

U.S. PATENT DOCUMENTS

| | | | |
|---|---|---|---|
| 8,273,712 B2 | 9/2012 | Kelly | |
| 2015/0342961 A1* | 12/2015 | Xue | A61K 31/5575 514/252.18 |

FOREIGN PATENT DOCUMENTS

| | | |
|---|---|---|
| EP | 0326149 | 8/1993 |
| WO | 2011/068896 | 6/2011 |

OTHER PUBLICATIONS

Angstreich et al. Effects of imatinib and intereron on primitive chronic myeloid leukaemia progenitors. Brit J Haematol 130: 373-381, 2005.*
Bedi et al. Growth factor-mediated terminal differentiation of chronic myeloid leukemia. Cancer Res 54: 5535-5538, 1994.*
Buchner et al. The role of GM-CSF in the treatment of acute myeloid leukemia. Leuk Lymphoma 11 Suppl 2: 21-24, 1993 (abstract only).*
Cortes et al. GM-CSF can improve the cytogenic response obtained with interferon-alpha therapy in patients with chronic myelogenous leukemia. Leukemia 12: 860-864, 1998.*
Disis et al. Granulocyte-macrophage colony-stimulating factor: an effective adjuvant for protein and peptide-based vaccines. Blood 88(1): 202-210, 1996.*
Gluckman et al. Use of prostaglandin E1 for prevention of liver veno-occlusive disease in leukaemic patients treated by allogeneic bone marrow transplantation. Brit J Haematol 74: 277-281, 1990.*
Iwata et al. Intraportal perfusion of prostaglandin E1 attenuates hepatic postischaemic microcirculatory impairments in rats. J Gastroenterol Hepatol 14: 634-641, 1999.*
Pimilla-Ibarz et al. The biological basis for immunotherapy in patients with chronic myelogenous leukemia. Cancer Control 16(2): 141-152, 2009.*
Provastin VR (alprostadil) datasheet from Pfizer, Apr. 2013.*
Witz et al. Priming with GM-CSF for acute myelogenous leukemia (AML): Goelam data. Ann Hematol 83 (Suppl 1): S55-57, 2004.*
Zeidner et al. Granulocyte-macrophage colony stimulating factor (GM-CSF) enhances the clinical responses to interferon-alpha (IFN) in newly diagnosed chronic myeloid leukemia (CML). Leukemia Res 38: 886-890, 2014.*
International Search Report issued in corresponding International Patent Application No. PCT/EP2015/001979 (with English translation) dated May 4, 2015 (10 pages).
Grabrucker et al., "The Quality and Quantity of Leukemia-derived Dendritic Cells From Patients With Acute Myeloid Leukemia and Myelodysplastic Syndrome are a Predictive Factor for the Lytic Potential of Dendritic Cells-primed Leukemia-Specific T Cells," Journal of Immunotherapy, vol. 33, No. 5, 2010, pp. 523-537.

(Continued)

*Primary Examiner* — Bridget E Bunner
(74) *Attorney, Agent, or Firm* — Sand, Sebolt & Wernow Co., LPA

(57) ABSTRACT

A method for selecting an immunomodulatory kit, selected for an individual patient, for use in the treatment of patients suffering from myeloid leukemias. Different kits are available for selection and ex vivo testing which are composed of substances that have different immunomodulatory effects on leukemia cells. Each kit particularly contains GM-CSF and one (or two) more substances, selected from PICIBANIL, PGE1, PGE2, CALCIMYCIN and TNFα, as well as pharmaceutically acceptable adjuvants. The clinical aim is to modify, once the individually selected immunomodulatory kits were administered, blast cells in the body of the patient such that they turn into a "vaccine" which is able to activate the immunoreactive cells (of the patient or of the stem cell donor) in the body against blast cells.

Figure 1A:
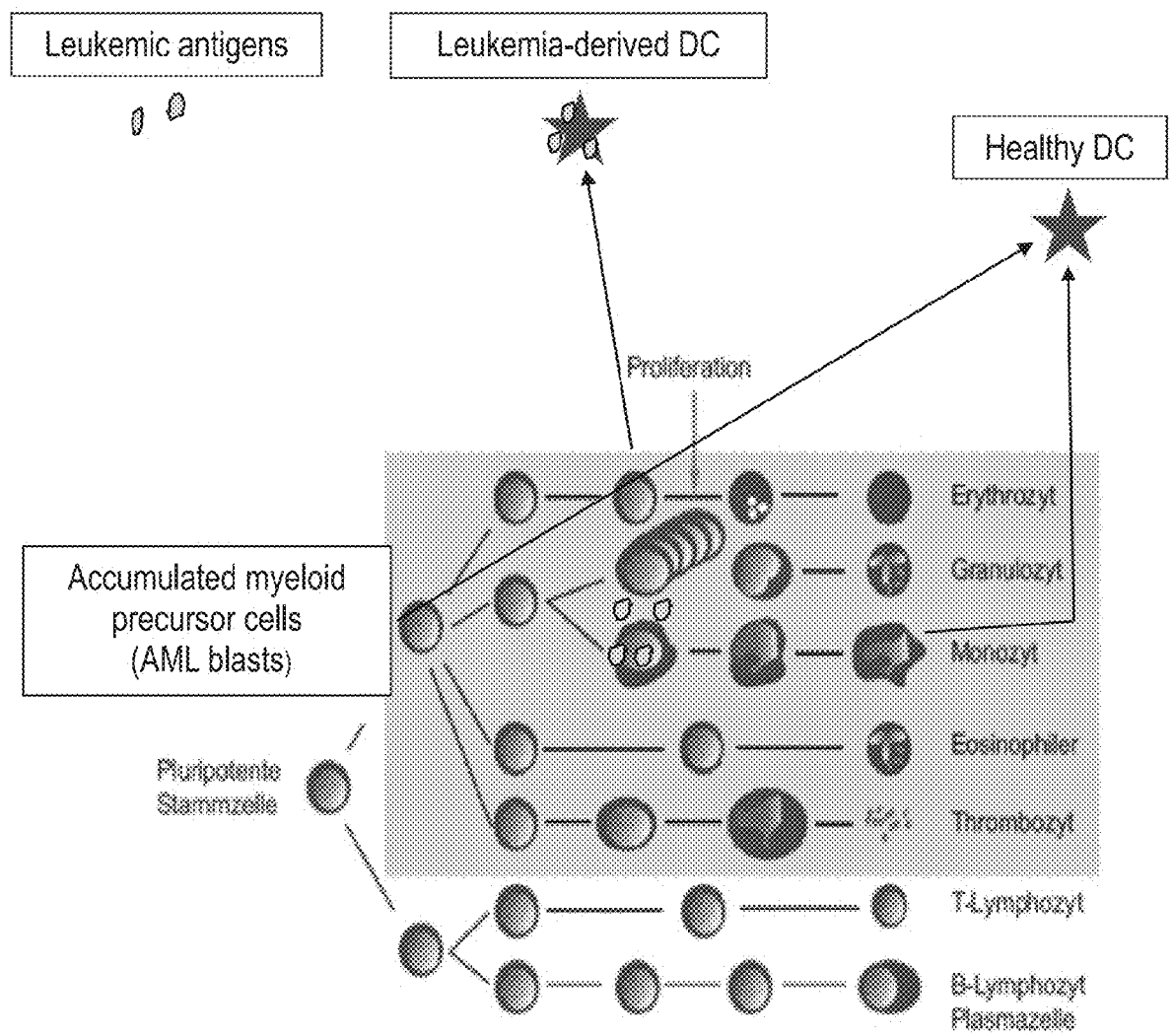

10 Claims, 15 Drawing Sheets
(4 of 15 Drawing Sheet(s) Filed in Color)

(56) References Cited

OTHER PUBLICATIONS

Kremser et al., "Dendritic Cells (DCs) Can Be Successfully Generated From Leukemic Blasts in Individual Patients With AML or MDS: An Evaluation of Different Methods," Journal of Immunotherapy, vol. 33, No. 2, 2010, pp. 185-199.
Roddie et al., "Phase 1/11 study of vaccination with dendritic—like leukaemia cells for the immunotherapy of acute myeloid leukaemia," British Journal of Haematology, vol. 133, No. 2, 2006, pp. 152-157.
Schick, J., Pradiktive Relevanz regulatorischer T-Zellsubpopulationen nach Stimulation mit dendritischen Zellen leukamischer Abstammung fur die antileukamische T-Zellantwort, Dissertation 2014, LMU Munchen, URL: http://edoc.ub.uni-muenchen.de/16887/ (veroffentlicht May 14, 2014; rescherchiert am Apr. 28, 2015 (English Abstract attached).
Schurch et al., "Dendritic cell-based immunotherapy for myeloid leukemias," Frontiers in Immunology, vol. 4, Article 496, 2013, pp. 1-16.
Becher et al. GM-CSF: from growth factor to central mediator of tissue inflammation. Immunity 45: 963-973, 2016.
Gasson, J.C. Molecular physiology of granulocyte-macrophage colony-stimulating factor. Blood 77(6): 1131-1145, 1991.
Kirtland, S. J. Prostaglandin E1: A review. Prostaglandins Leukot Essent Fatty Acids 32(3): 165-174, 1988.
Steinbrink et al. Induction of dendritic cell maturation and modulation of dendritic cell-induced immune responses by prostaglandins. Arch Dermatol Res 292: 437-445, 2000.

\* cited by examiner

FIG.2A

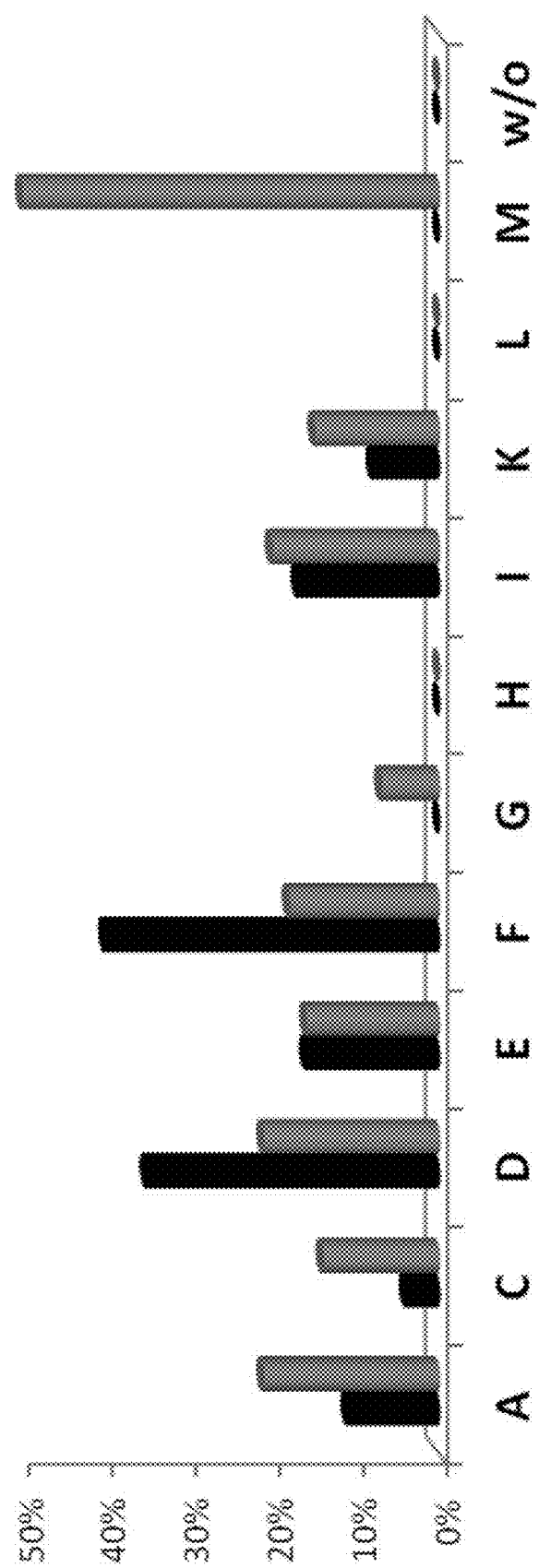

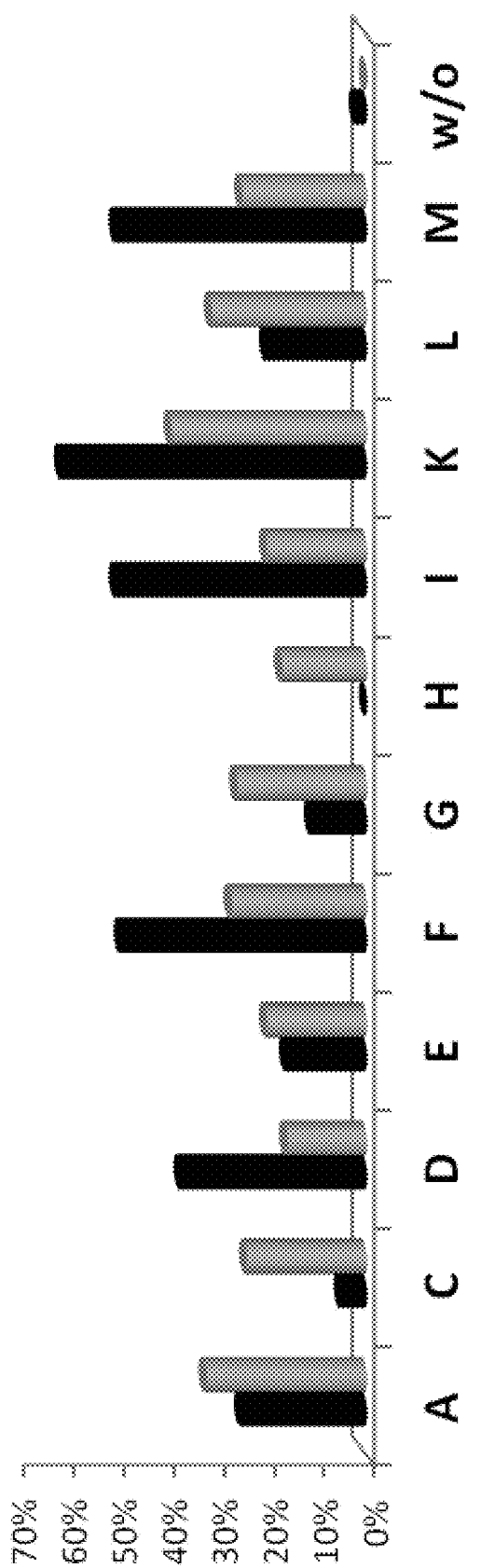

| | % DC/cellsus | % DCleu/cellsus | % DCleu/DC | % DCmig/DC |
|---|---|---|---|---|
| 'excellent' | >25 | >15 | >25 | >30 |
| 'excellent/high' | ≥25-20 | ≥15-12 | ≥25-16 | ≥30-21 |
| 'high' | ≥19-14 | ≥11-8 | ≥15-11 | ≥20-15 |
| 'sufficient' | ≥13-10 | ≥7-5 | ≥10-5 | ≥14-10 |
| 'Not sufficient' | <10 | <5 | <5 | <10 |

FIG.3C

| | 'best' or 'second best' DC-method' in comparison | | | 'excellent' or 'high' quality (including DC$_{mig}$ data) | | | 'excellent' or 'high' quality (excluding DC$_{mig}$ data) | |
|---|---|---|---|---|---|---|---|---|
| D | best/secondbest | 56* | K | 'excellent/high' | 83* | K | 'excellent/high' | 77* |
|   | Not successful | 12* |   | Not successful | 0* |   | Not successful | 0* |
| F | best/secondbest | 58* | F | 'excellent/high' | 81* | M | 'excellent/high' | 75* |
|   | Not successful | 6* |   | Not successful | 3* |   | Not successful | 25* |
| M | best/secondbest | 50* | M | 'excellent/high' | 75* | I | 'excellent/high' | 63* |
|   | Not successful | 25* |   | Not successful | 25* |   | Not successful | 0* |
| I | best/secondbest | 37* | D | 'excellent/high' | 67* | D | 'excellent/high' | 50* |
|   | Not successful | 0* |   | Not successful | 11* |   | Not successful | 7* |
| A | best/secondbest | 32* | I | 'excellent/high' | 70* | F | 'excellent/high' | 47* |
|   | Not successful | 18* |   | Not successful | 0* |   | Not successful | 7* |
| K | best/secondbest | 23* | A | 'excellent/high' | 57* | A | 'excellent/high' | 27* |
|   | Not successful | 0* |   | Not successful | 17* |   | Not successful | 16* |

FIG. 3D

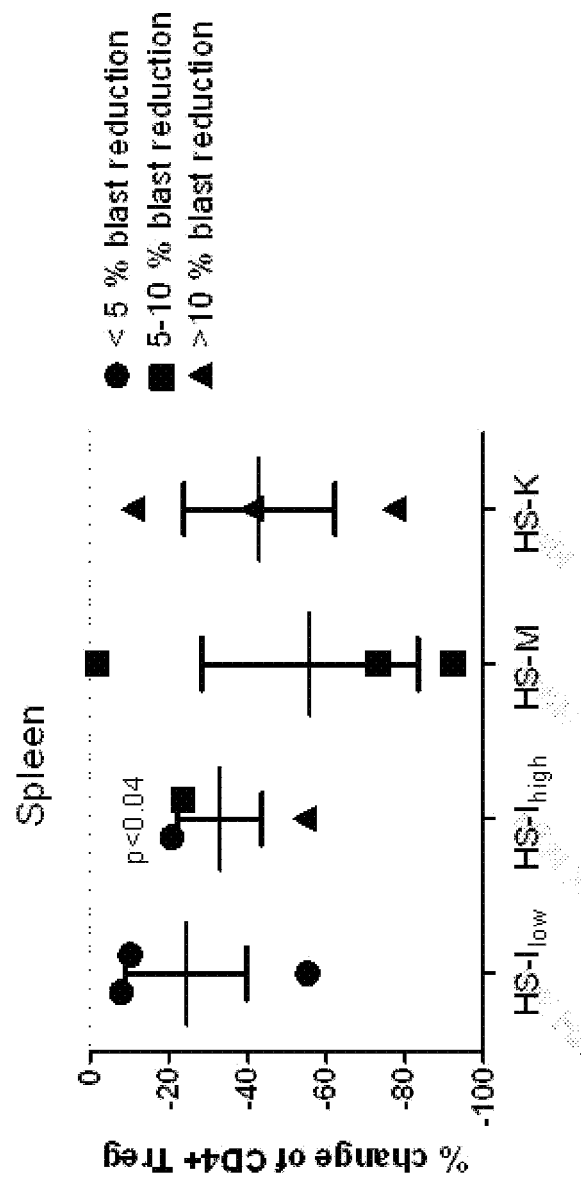

USE OF IMMUNOMODULATORY KITS FOR IMMUNOTHERAPEUTIC TREATMENT OF PATIENTS WITH MYELOID LEUKEMIAS

CROSS REFERENCE TO RELATED APPLICATIONS

This application is a continuation of U.S. patent application Ser. No. 15/517,627 filed on Apr. 7, 2017, which is a National Stage Entry of PCT Patent Application No. PCT/EP2015/001979 filed on Oct. 8, 2015, which claims priority from DE 102014014993.5 filed Oct. 9, 2014; the disclosures of which are incorporated herein by reference.

SUMMARY OF THE INVENTION

The present invention relates to a method for selection of a patient-individually selected immunomodulatory kit for use in the treatment of patients with myeloid leukemias. For selection and ex vivo testing, there are different kits, composed of different substances immunomodulatory active on leukemic cells. In particular, the invention relates to a kit containing GM-CSF and a further agent selected from PICIBANIL, PGE1, PGE2, CALCIMYCIN and TNFα, as well as pharmaceutically compatible adjuvants.

Clinical goal is to modify blasts in the patient's body after administration of the individually pre-selected immunomodulating kits so that they become a 'vaccine' that can selectively activate immunoreactive cells (of the patient or the stem cell donor) in the body against blasts.

I. TECHNICAL FIELD OF THE INVENTION

Immunotherapeutic treatment of patients with myeloid leukemia.

The present invention relates to various kits composed of various immunomodulatory agents for use in the treatment of patients with myeloid leukemias. In addition, the present invention relates to a method for selecting a suitable kit for use in the treatment of patients with myeloid leukemias.

II. BACKGROUND OF THE INVENTION

Clinic:

Myeloid leukemia, such as acute myelogenous leukemia (AML), myelodysplasia (MDS), or chronic myeloid leukemia (CML), are clonal haemopoietic disorders that go along with a pathologically enhanced cell proliferation and disturbed differentiation of cells related to immune defense. Depending on the subtype of the disease, these diseases are associated with a poor prognosis, especially in refractory/recurrent stages; about 80% of successful chemotherapies suffer a relapse of their disease in the following two years.

Therefore, there is an urgent need for innovative immunotherapeutic treatment approaches (Reagan: Cellular immunotherapy for refractory hematological malignancies. J Transl Med. 19, 11, 150 2013). The allogeneic stem cell transplantation (SCT) is the most effective antileukemic therapy, which is reserved for younger patients, however. In addition to intensive (radio) chemotherapy, the allogeneic graft-versus-leukemia (GvL) immune effect applies as a therapeutic principle. According to current knowledge, the GvL effect is mediated primarily by T-lymphocytes of the donor. Complications after therapy, caused by the lack of regeneration-/immunocompetence of blood cells, are infections, bleeding, anemia, or relapse, caused by recurrent blasts. In patients with alloSCT, acute autoimmune responses to recipient cells ('graft versus host' (GvH) reactions) can occur, caused by immunoreactive cells of the stem cell donor. It can lead to severe inflammatory reactions to the skin, intestines and vascular systems e.g. Veno occlusive disease (VOD).

In addition to T cells, also dendritic cells (DC) play a decisive role as professional T cell stimulators in the mediation of immune reactions. In principle, therapeutic effects (blast reduction) after vaccination of AML patients with antigen-pulsed DC (for example WT1) could already be shown. However, this strategy is reserved only for patients with a defined HLA type (usually HLA A2) and knowledge of a leukemia-associated antigen (e.g. WT1).

Compared to lymphocytic leukemia forms treatment responses of myeloid leukemia (CML, AML, MDS) were ascribed to the capability of myeloid blasts to differentiate to leukemia-derived DC (DCleu) and improved presentation of leukemia-associated antigens (Schmid: Low-dose ARAC, donor cells, and GM-CSF for treatment of recurrent acute myeloid leukemia after allogeneic stem cell transplantation. Leukemia; 18(8):1430-3, 2004). Based on this concept, in the treatment of AML-relapse following allogeneic SCT, GM-CSF has been systematically used in some patients to induce differentiation of myeloid blasts to antigen-presenting cells in vivo. The state of the art is that cytokines such as GM-CSF or kit-ligand alone or in combination with other stem-cell-like cytokines (e.g. G-CSF) or various small molecules are administered to the patient as 'stem cell regeneration cytokines', aiming on the body to mobilize stem cells from the bone marrow into the blood and therefore (e.g. after chemotherapy or organ damage) regenerates blood cells (Besmer: Composition of cKitligand, GM-CSF and TNFa and Method of use, U.S. Pat. No. 6,001,803; 1999).

$DC/DC_{leu}$ Generation Ex Vivo:

A number of different methods are suitable for the ex vivo differentiation of DC for AML patients, but successful differentiations are not possible with all methods in each individual case. A strategy has been developed to obtain DC (especially mature DC and DCleu) in cell culture with the best of three pre-tested methods (CA, MCM, PICI, INTR) in each individual patient (Kremser/Schmetzer: Dendritic cells can be successfully generated from leukemic blasts in individual patients with AML or MDS. J. Immunotherapy 33:185-199, 2010); Dreyssig/Schmetzer: Various 'Dendritic Cell Antigens' are already expressed on uncultured Blasts in Acute Myeloid Leukemia and Myelodysplastic Syndromes. Immunotherapy 3(9), 1113-1124 (2011); Schick/Schmetzer: Antileukemic T-cell responses can be predicted by the composition of specific regulatory T-cell subpopulations. J. Immunotherapy, Vol. 36, 4, 223-237; (2013)).

Table 1a (columns a1-a4) shows the above-mentioned methods: they contain numerous active substances in combination: different cytokines and 'risk factors and maturation factors', which differentiate DC from monocytes or blasts (initially in the serum-free cell culture from mononuclear cells (MNC)). In each method, the active compounds indicated in Table 1a were used in each case in combination. The leukemic origin of DC was demonstrated by detection of the clonal leukemia-associated chromosomal aberrations IN the DC by fluorescence in situ hybridization (FISH) or by the flow cytometric detection of the individual blast antigen pattern on the cell surface of the DC.

The advantage of producing DC directly from leukemic blasts is that tumor antigens need not be known because the blasts are converted to DCleu and present the entire leukemic antigen spectrum of each individual patient. Using these methods, it was shown that none of the DC generation methods produces a pure culture of DCleu: approximately 45-55% of the obtained DCs are proven to be leukemia-derived. On the other hand, approximately 50-60% of the available blasts are convertible to DCleu. This means that although DC of leukemic origin are generated regularly, not all blasts are converted to DC.

Figure 1B:
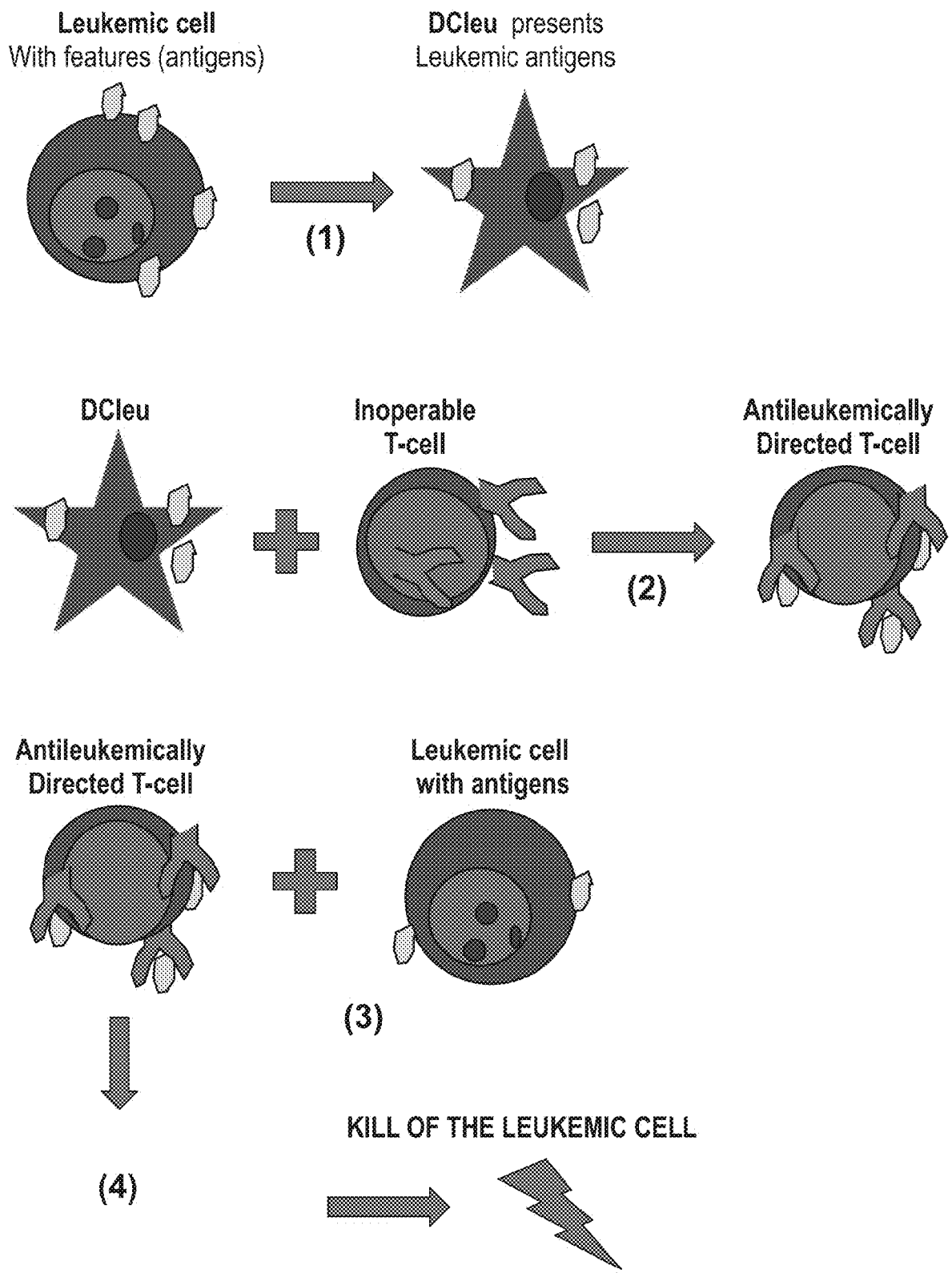

FIG. 1A shows schematically, using the example AML, that, in addition to normal DC (from monocytes or stem cells), DCleu are also formed, that is, that blasts are 'redifferentiated' to DC T Cell Stimulation with DC/DCleu EX VIVO:

By ex vivo stimulation experiments of T-cells with DC/DCleu, anti-leukemic T-cells can be produced (compared to unstimulated or blast-stimulated T-cells) (Grabrucker/Schmetzer: The Quality and Quantity of Leukemia-Derived Dendritic Cells DC). Patients with acute myeloid leukemia and myelodysplastic syndrome are a predictive factor for the lytic potential of DC-primed leukemia-specific T-Cells J Immunotherapy 33, 5, 523-537, 2010). FIG. 1B shows the experimental setup for such stimulation experiments in mixed lymphocyte cultures (MLC): myeloid leukemic cells (e.g. AML cells) can be converted to DCleu (by DC methods/kits) '(b1). These DCleu 'present' all AML antigens of the patient and thereby stimulate T cells (b2), which in turn can recognize and kill AML cells (b3). Furthermore, an immunological memory is applied (b4).

T cell stimulation experiments in mixed lymphocyte cultures (MLC) have shown that DC-stimulated T cells proliferate not only better than blast-stimulated or unstimulated T cells, but also more frequently and show more effectively leukemia cytotoxic efficacy (albeit not in every case). In this case, both the quality of the DC (e.g. maturity, proportions, leukemia-derived DC', etc.), as well as the composition of the resulting T cells (e.g. proportions of CD4 or CD45RO+ non-naïve, CD4:CD8 relations, regulatory, ß-integrin-expressing T-cells, etc.) as well as soluble factors in the cell culture supernatant (e.g. IFNγ, IL-6, CXCL8, CCL2) are predictive for the function of DC-stimulated T cells as well as for the response of patients to immunotherapies (SCT or DLI therapy). In T-cell clonality studies it was shown that the T cell repertoire is restricted after DC/DCleu-'compared to blast stimulation: some CD4/CD8 clones were preferably clonally amplified, which indicates that DC/DCleu "direct, focus and reinforce" immuno-reactions. It is interesting to note that an identical T cell clone (identical T cell receptor Vβ sequence) could be detected by Spectratyping in combination with sequence analyzes after DC stimulation ex vivo as well as in vivo from T cells of a patient after SCT. This means, that with DC cultures not only simulate in vivo processes, but these clones can also be functionally analyzed (e.g. by functional blast lyse test).

Since the antileukemic function of the T cells in the body of AML patients is crucial for the maintenance of a long-lasting remission, an optimization of the antileukemic T cell function as well as the generation of T memory cells (which can at any time provide specific effector cells) would be of great clinical value to control (residual) leukemic cells in the patient's body.

It is unclear whether after DC stimulation an expansion (of many or less) specific antileukemic T cell populations (in vivo, in vitro) takes place, whether an immunological memory is applied, whether the function of specific T-cells is influenced by soluble factors and above all, whether the antileukemic function in vivo is sufficient to achieve or maintain remissions. Therefore, in addition to immunotherapies, a targeted 'monitoring' (identification, quantification) of relevant T cell populations must be carried out ex vivo or in vivo by using suitable methods (flow cytometry, molecular biology).

III. SUMMARY OF THE INVENTION

The object of the present invention is to modify blasts of patients with myeloid leukemias with immunomodulating methods in vivo in such a way that they become a 'vaccine' which can specifically activate immunoreactive cells (of the patient or the stem cell donor) against blasts. This object is achieved by the features of the independent claims. Further embodiments of the invention are specified in the dependent claims.

The present invention allows the alternative use of different kits, composed of various immunomodulatory agents, for the treatment of patients with myeloid leukemia—in the sense of personalized medicine. First, in a cultured system with clotting-inhibited whole blood samples of the leukemia patients in blast-rich stages from 6 alternative kits, the patient's individual best is selected: the best kit is the best conversion of blasts into leukemia-derived dendritic cells (DCleu) as antigen presenting cells without induction of blast proliferation and at the same time the best antileukemic T cell activation.

IV. DESCRIPTION OF ILLUSTRATIONS AND TABLES

The patent or application file contains at least one drawing executed in color. Copies of this patent or patent application publication with color drawing(s) will be provided by the Office upon request and payment of the necessary fee.

FIG. 1 comprises FIG. 1A and FIG. 1B: DC/, leukemia-derived DC (DCleu)-mediated antileukemic T cells FIG. 1A: DC are produced from stem cells or monocytes in the healthy organism; AML blasts can also be differentiated to 'leukemia-derived' DC (Dcleu); In other words, DCleu arise from 'redifferentiated' AML blasts FIG. 1B: Antileukemically active, DC/DC-stimulated and activated T cells (ex vivo/in vivo)

Figure 2A:
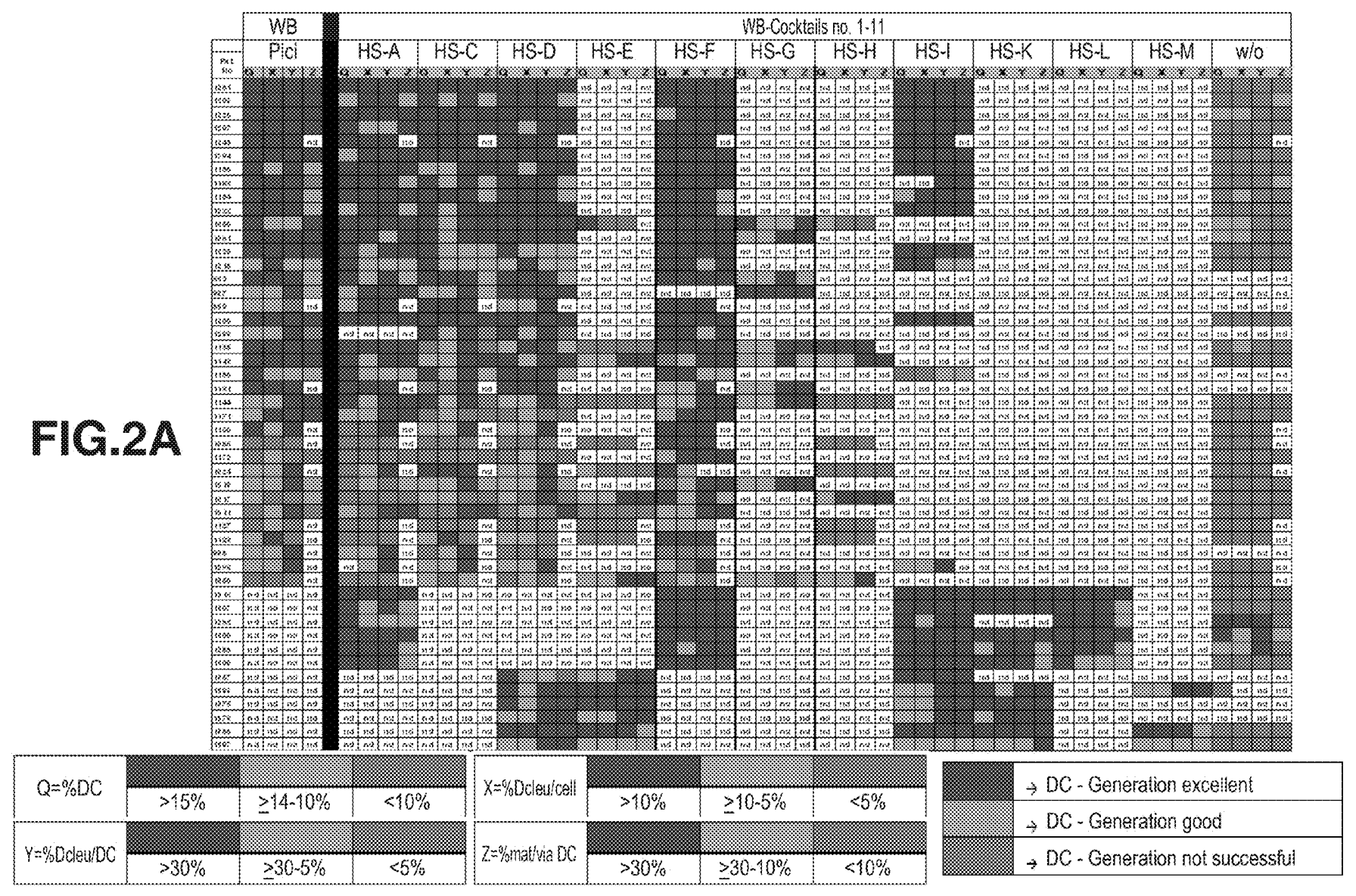
Figure 2B:
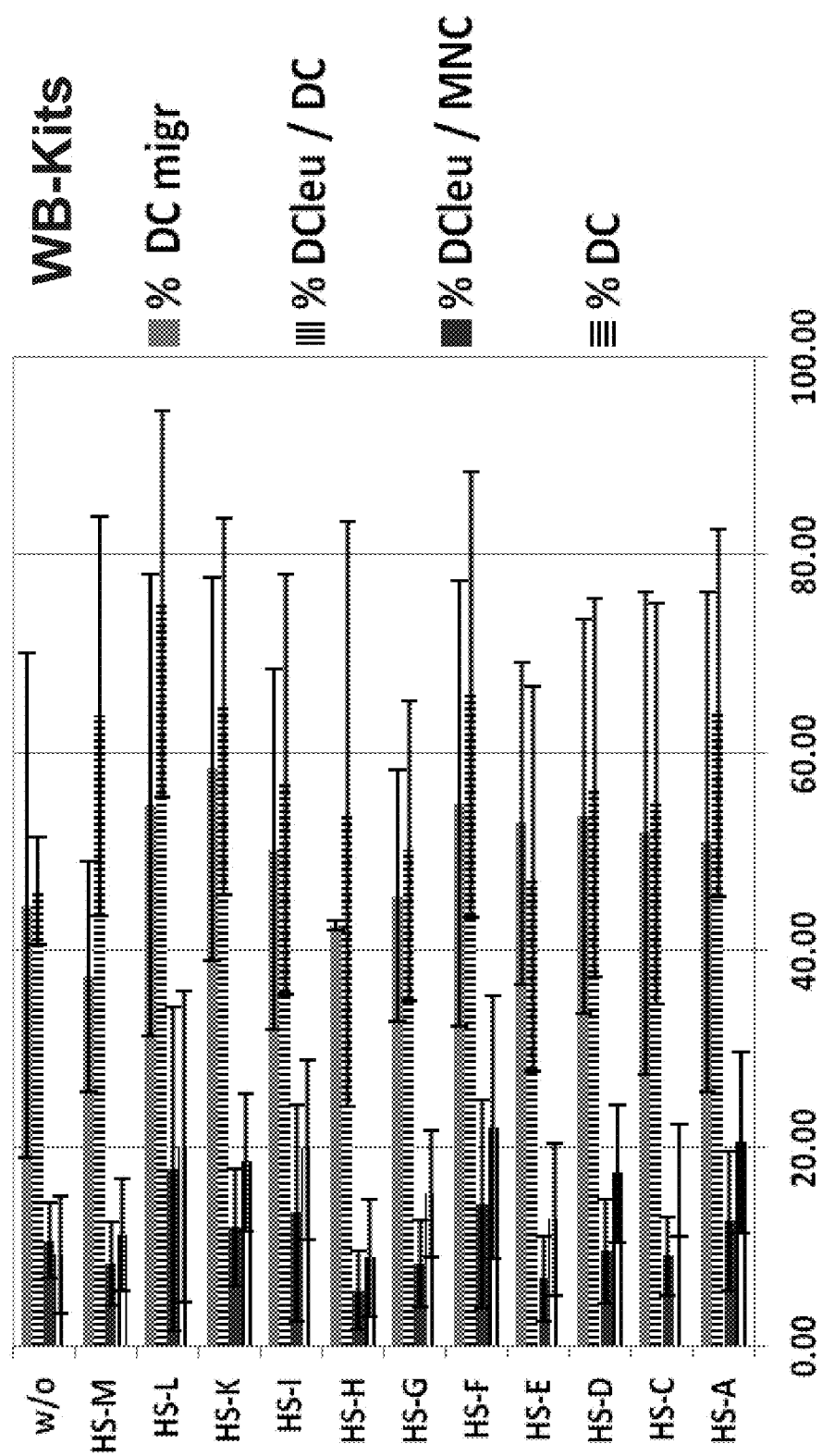

FIG. 2 comprises FIG. 2A and FIG. 2B: $DC/DC_{leu}$ can be generated from AML blast-containing WHOLEBLOOD (WB) samples with standard DC differentiation methods (CA, MCM, PICI, INTR) as well as with 'Kits' (patient/individually selected)

FIG. 2A: $DC/DC_{leu}$ generation from WB using standard procedures (e.g. Pici, left side) and kits (right side)

FIG. 2B: Comparable average amounts of DC subtypes can be generated with all kits. (DC migr: migratory DC (CCR7+); DCleu/DC: proportions of DC leukemic lineage in the DC fraction; Dcleu/cell: proportions of DC leukemic in the cell fraction; and w/o: WB control without added kits)

FIG. 3 comprises FIG. 3A, FIG. 3B, FIG. 3C and FIG. 3D: Ranking list: Selection of the best WB kit method for generating $DC/DC_{leu}$ subtypes in individual AML patients: the percentage frequencies of a successful $DC/DC_{leu}$ generation with individual kits are shown FIG. 3A: RANKING: 'best or second best DC method' compared to at least 3 other kits FIG. 3B: RANKING: DC method with 'excellent or high quality' (criteria see FIG. 3C.)

FIG. 3C: Criteria for successful DC generation

FIG. 3D: Selection of the 6 best kits according to RANKING criteria

Figure 4A:
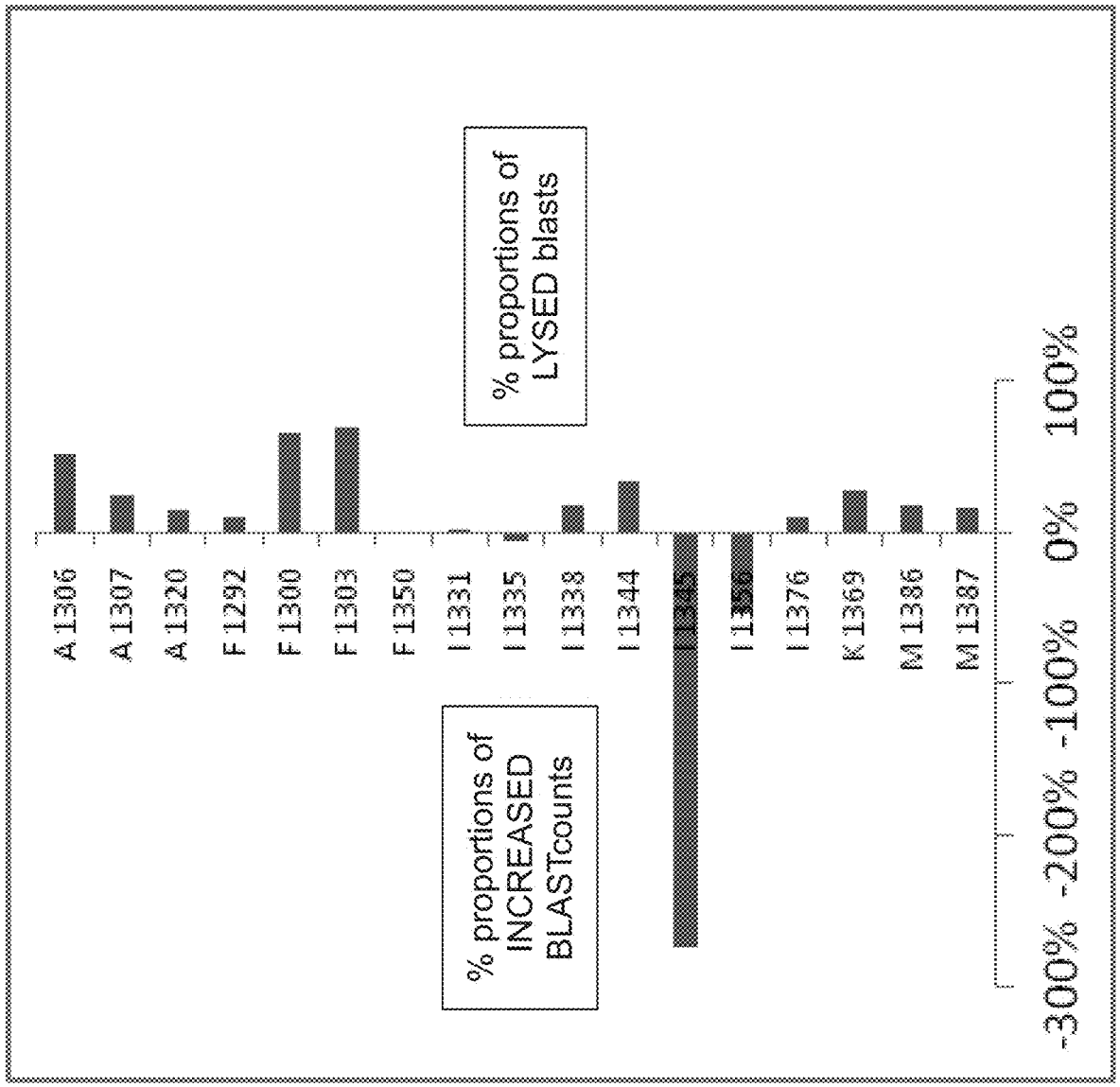
Figure 4B:
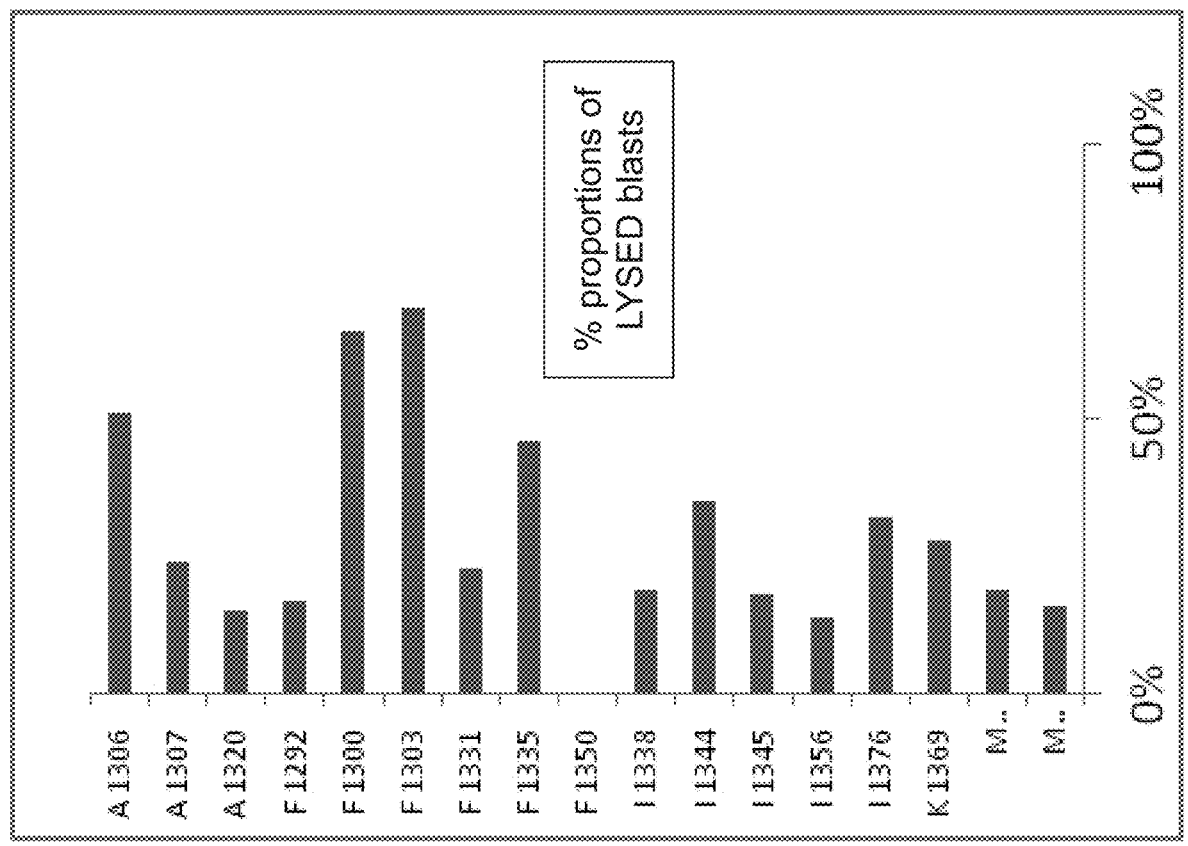
Figure 4C:
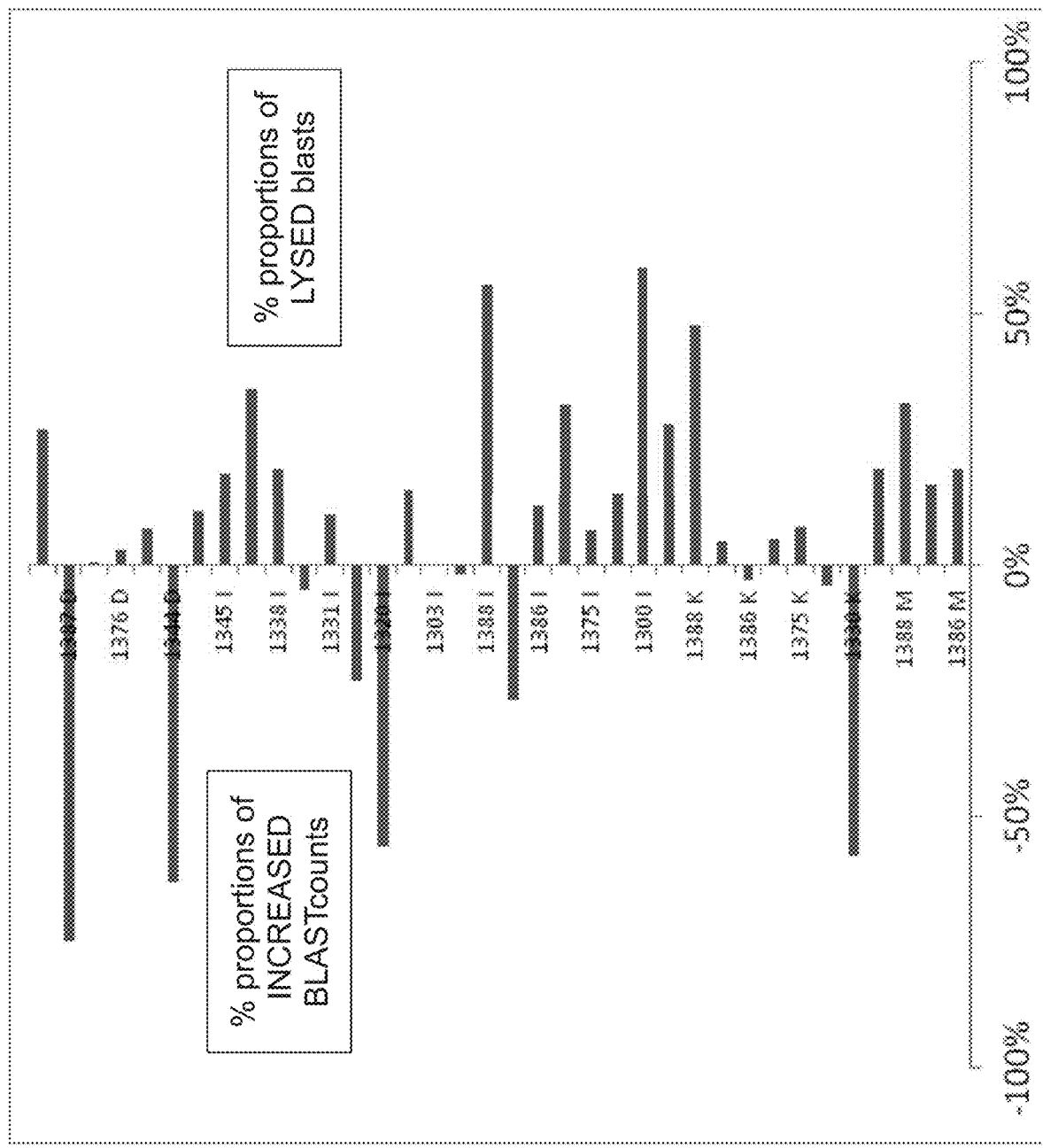

FIG. 4 comprises FIG. 4A, FIG. 4B, and FIG. 4C: Antileukemic-blast-lytic activity of T cells that were stimulated with KIT-TREATED (HS-D, F, I, M, K, A) compared to untreated AML WB samples FIG. 4A: Selection according to the patient's individual best lytic value FIG. 4B: Selection according to the patient's individual greatest difference to the WB control lysis value FIG. 4C: Selection of HS-D, I, K, M treated WB samples compared to the WB control FIG. 5 comprises FIG. 5A, FIG. 5B, FIG. 5C and FIG. 5D: Treatment of BNML rats with kits leads to reduction in blast proportions and changes in Tcell compositions in blood and spleen compared to placebo control FIG. 5A: Experimental design of rats' treatment FIG. 5B: Blast reduction in blood (left) and spleen (right)

Figure 5A:
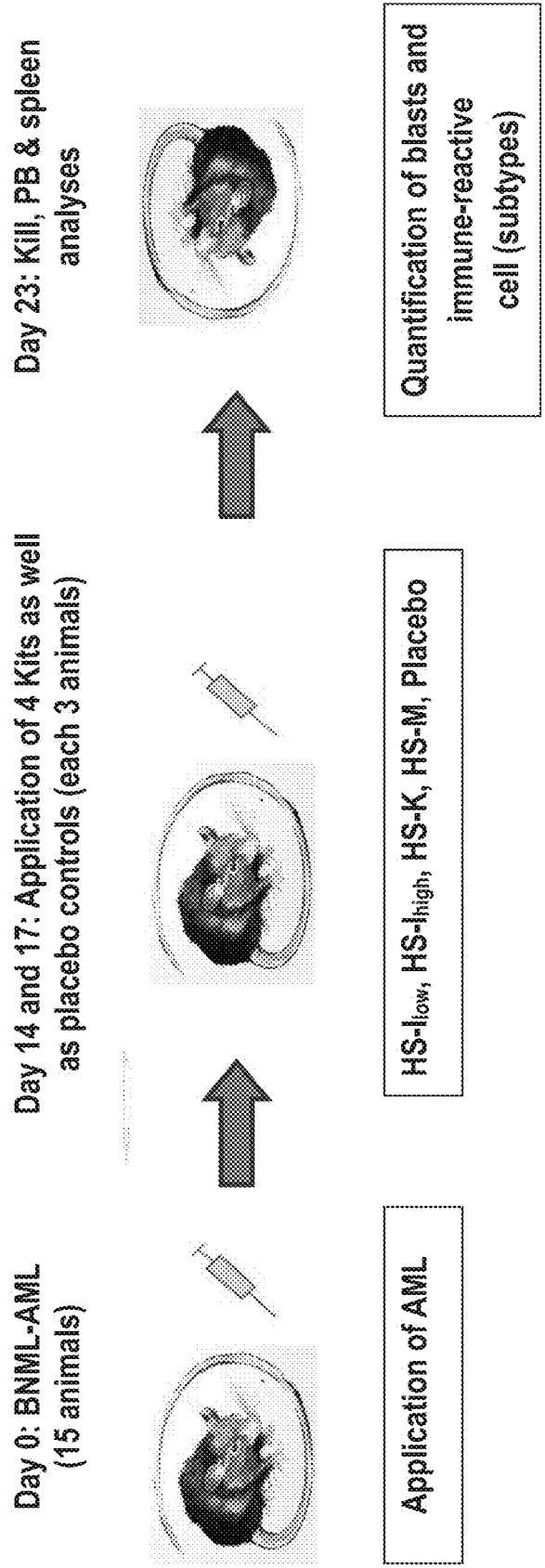
Figure 5B:
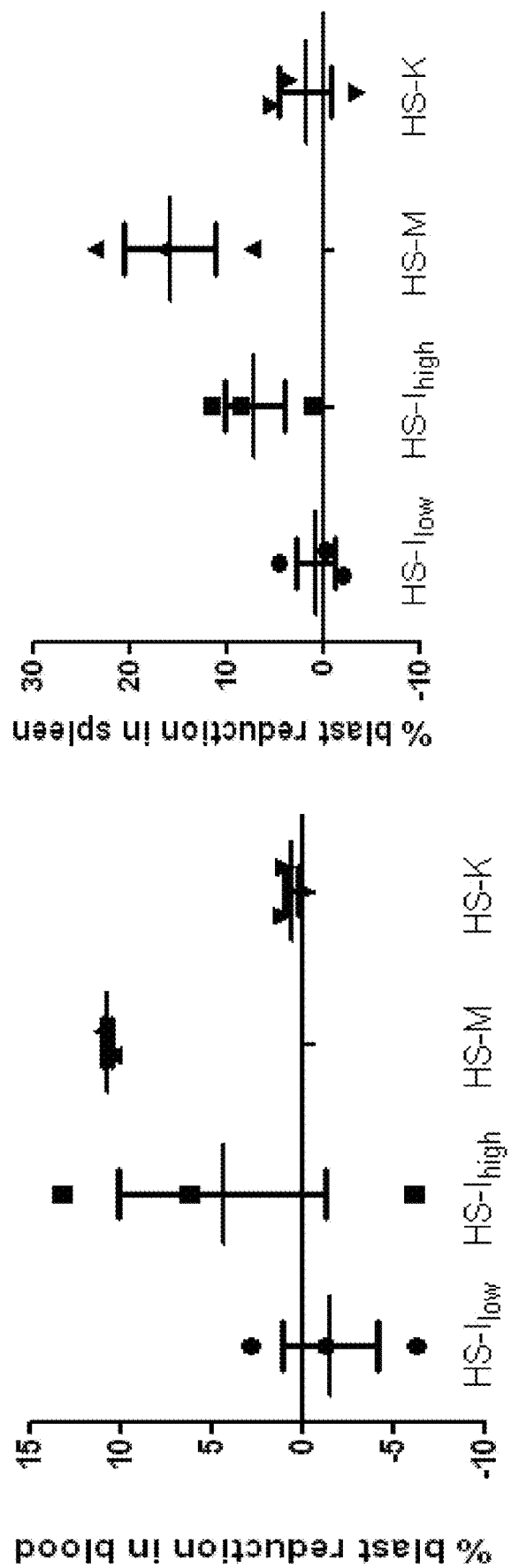
Figure 5C:
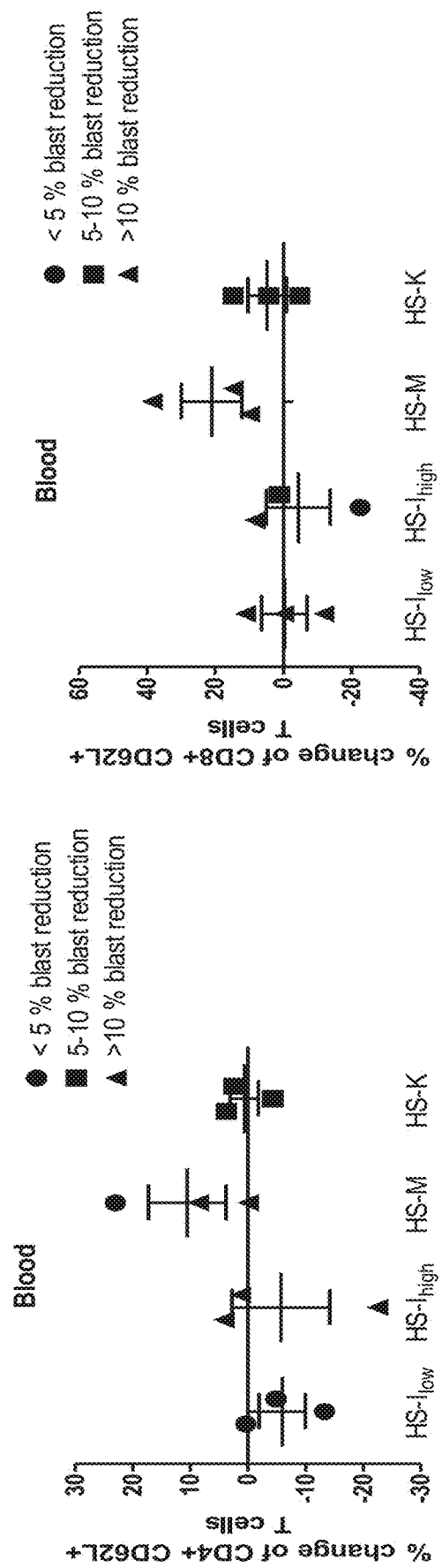

FIG. 5C: Increase of CD62L+(Tmem): CD4+(left) and CD8+(right side) in blood and spleen FIG. 5D: Reduction of CD4+CD25+FoxP3+Treg in the spleen Table 1: Generation of DC/DCLeu from AML blast-containing mononuclear cells (MNC) or whole blood (WB) cells with different DC differentiation methods or specific kits
a) DC differentiation methods or kits for the generation of DC/DC cells from blast-containing MNC (a1-a4) or WB (a1-a5)
b) Advantages and value of DC generation from whole blood samples Table 2: Ingredients in the kits for the immunomodulation of AML blasts Table 3: Composition of the tested kits

V. DETAILED DESCRIPTION OF THE INVENTION

The invention presented below in the example of the AML qualifies likewise in patients with other myeloid leukemia. According to the present invention, in vitro, a minimized combination of clinically approved "immunomodulators" was developed and tested. This was done with a test model with "heparinized whole blood (WB) samples" (taken in heparin tubes with standardized heparin addition): WB contains all soluble and cellular components of patients with leukemic disease and also all cellular and soluble influencing variables on the DC generation.

It is also possible to determine in vitro at the same time whether DC differentiation in vivo is possible and differentiation resistances of the cells can be overcome and thus a functioning humoral and cellular immunity can be (re-)established in the patient. Very cell-rich WB samples were diluted with ca 30-50% serum-free medium (X-vivo) in order to guarantee the comparability of the individual cases. Table 1b shows advantages of generating DC/DCleu from WB: all cell types and soluble factors present in the body can be detected in their "natural environment". Functionality tests are tested close to the clinical reality and can yield finally conclusions about biological correlations and reaction profiles compared to results with mononuclear cells, the normally used leukocyte fraction for examinations.

Similar proportions of DC (subtypes, determined by flow cytometry) were obtained both from WB and from MNC of patients with leukemic diseases with the standard methods (CA, PICI, MCM or INTR, Table 1a) what means that a WB model is in general suitable for inducing the modulation of blasts ex vivo, to evaluate the convertibility of blasts to DCleu. Moreover it is a good physiological model to test how successful immunomodulation is. The next step it was shown that the generation of DC (subtypes) from WB with the standard methods was similar to that with minimized Kits consisting of 1-3 clinically approved immunomodulators, from WB while culture controls without the addition of kits, did not give rise to DCs from the blasts (the composition of the kits is given below).

FIG. 2A shows results of the DC generation from WB using standard method, Pici '(left side) compared to WB with kits (right side): many of the 11 kits tested yield similar amounts of DC subtypes from WB of leukemic patients as with standard methods. Average (see bar graphs FIGS. 2A and 2B shows similar levels of DC (subtypes (see table):% DC ('Q'), mature/migratable DC ('Z'), DCleu converted to blasts, DCleu in the entire cell fraction ('X') related to all DC ('Y')) from WB: With at least one method a good DC generation was possible for each patient. Culture controls without the addition of kits are usually unsuccessful. Furthermore, it is also apparent that not every kit is equally suitable for individual patients to generate DC (subtypes) (see table and FIG. 2A).

Thus, a WB method is a good physiological model for DC/DCleu generations, whereby patient-specific differences are recognizable: individual kits are better than others suitable to generate DC (subtypes).

Several kits were (comparatively) tested within the scope of the present invention. All substances are approved for the application in humans and are regularly used in patients with other indications than listed below. A number of individual substances as well as their combinations were used for this purpose regarding their abilities to generate DC (subtypes), to stimulate leukemic cells to proliferate, or the resulting DC products were finally tested for the ability to activate anti-leukemic T cells.

Table 2 shows the used individual ingredients, their biological/clinical effect and previous areas of clinical applications: In summary, GM-CSF, IFNα, TNFα, and PICIBANIL are used as immunomodulators and immunostimulants, for hematopoietic regeneration and systemic application for the treatment of various diseases (PICIBANIL is also applied locally in tumors). PGE 2 is used in high concentrations to initiate the birth and is administered vaginally locally or systemically. Due to its vasodilatory properties, PGE 1 is systematically used for example for treatment of VOD disease or of ischemias on extremities. TNFα can be administered systemically but also locally in soft tissue tumors in high concentrations. CALCIMYCIN is not yet used systematically in human beings (although experience from animal experiments are available), but is used ex vivo for the treatment of oocytes before in vitro fertilization.

DC/DCleu—Generation Ex Vivo—Selection of the Best Kits (Ranking):

It was shown that not every Kit is equally well suited for DC (subtype) generation in individual patients (FIG. 2A). Therefore, we have created a "ranking list" for DC generation kits where the percentual values of DC, DCleu as well as mature migratory DC (DCmig) were used for the evaluation: FIG. 3A shows the frequencies of individual kits (composition see Table 3) being BEST OR SECOND best DC generation method compared to at least 3 other kits: HS-F, D, M, I, A, K ranked among all as best or second best methods, while the remaining kits ranked worse (FIGS. 3A and 3D). Alternatively, the frequencies are shown where DC-generation with kits was ranked as "EXCELLENT OR HIGH" (only oriented on DC subtype qualities), (FIG. 3B, criteria for the classification are shown in FIG. 3C).

Again the kits HS-K, F, M, I, D, A were ranked as 'EXCELLENT OR HIGH' DC generation if fractions of mature DCmig were included in the ranking (FIG. 3D, middle column) or excluded (right column).

All in all, our results showed that the first 6 kits mentioned are in any case capable to produce good DC/DCleu proportions, while the remaining kits or individual substances or controls only rarely produced sufficient amounts of DC at all.

Induction of Blast Proliferation Ex Vivo:

It must be excluded that administered kits to patients induce blasts' proliferation (in vivo). Blast proliferation-tests were performed in a WB-model on 51 samples: flow cytometry showed expression of the proliferation marker CD71 (transferrin receptor) on the blasts before (proportions of double CD71+ and blast-markers+blasts: 'CD71+Bla+/Bla+') and after influence of the kits (here the proportions of DCleu (expressing the blast markers) were excluded: CD71+Bla+DC−/Bla+)). Only cases with an expression of more than 10% of proliferation markers before culture were included in the analyses. CD71 is expressed regularly but not by all AML cases on the (unmodulated) blasts. Apart from a few exceptions (approximately 14% of the cases), no increase in CD71+, proliferating blasts was found after Kit-culture. Thus, with the exception of a few cases, it can be assumed that the proliferation of blasts under influence of kits will not be induced, however, the proliferation of blasts under the Influence of specific, patient-individually selected kits (in particular with regard to an in vivo application) should be studied. In the future, further methods to study proliferation (CFDA assay, Flow cytometric measurement of intracellular proliferation markers) should be applied in order to obtain a proliferation state in all patients before WB cultivation.

The used kits stimulate only in exceptionally cases (or only individual kits in individual patients) the blast proliferation in the WB-system. Therefore it is advisable to test the influence of different Kits on blasts in WB samples in all individual patients with leukemia and to choose the Kit for in vivo application which does not induce any blast proliferation and produces at the same time high DCleu proportions.

Preparation of Antileukemic T-Cells after Kit-Stimulation:

Ultimately, the antileukemic function of the T cells in the body is to maintain a long-lasting remission. Therefore, according to the invention, an optimization of the antileukemic T cell function and generation/reactivation of T-memory cells would be a great clinical benefit to fight (residual) leukemic cells in the patients' body. According to the invention it was therefore examined whether the Kit treatment of WB blasts leads to a better and more efficient antileukemic activity of T cells. FIG. 1B shows schematically how the ex vivo detection of the T cell function is performed: First, leukemic blasts are converted with a Kit to DCleu (b1). To the DC-containing (=Kit-modulated blasts) as well as to blasts without Kit treatment (control) in WB cultures isolated T cells from the patient were added and cultured together in mixed lymphocyte cultures for 7-10 days (b2). Finally, the antileukemic function of the cells is determined by the addition of (labeled) leukemic cells in a lysis-assay (flow cytometry): after incubation of these target cells with T-effector cells the decrease as well as the increase of blasts can be quantified (b3). Thereby it should be worked out whether the Kit treatment of WB blasts ends up in a better and more efficient antileukemic activity of T cells. In summary, FIG. 1B shows Antileukemic, blast-lytic activity of DC-(kit-generated)-stimulated T-cells (Scheme of our ex vivo/in vivo-targeted mechanisms)

(1) AML cells are convertible to DCleu (by DC methods/kits) ex vivo/in vivo
(2) T cell stimulation with DCleu (DCleu, present 'ALL AML antigens of the patient) results in antileukemically directed T cells
(3) antileukemically directed T cells recognize and kill AML cells
(4) Generation of immunological memory FIG. 4 shows results obtained with Kit-treated "Modulated WB blasts" in comparison to WB controls: due to the ranking criteria and the fact that the T cells are limited our trials functional tests were performed with the HS-A, F, D, I, K, M Kits. It can be seen that not always antileukemically effective Tcells are provided after Kit treatment of WB (T cells without blastlytic activity can also arise) and that the lytic efficiency of the resulting T-cells can be variable or individual best kits can be selected (FIG. 4A). In addition only WB ("blast-stimulated") Tcells can also be capable to give rise to antileukemically stimulated and cytotoxic Tcells (ex vivo), although less frequently and less efficiently. FIG. 4B shows that patient-specific Kits could be selected that improve the antileukemic function of the T cells most compared to the WB control. In almost all cases (at least) one Kit could be found, which leads to an improvement of the antileukemic Tcell function: selecting the best achieved LYSIS value after Kit influence and compared it with the WB control without addition of Kits at least one Kit could be always found (with the exception of some cases) in that the antileukemic function and at the same time an improvement over the control (without addition of Kit) could be shown. FIG. 4C shows (obtained in parallel) results with HS-D, I, K, M-treated kits. These 4 kits were selected preferentially and the kits HS-A and F were put on hold since the systemic application of TNFa or CALCIMYCIN-containing kits to patients is currently not allowed. It can be seen that kit-treated WB samples show differences in the provision of efficient antileukemic T cells. Therefore, a ranking of the antileukemic function was performed by us. This revealed that kits HS-I, K, F, M, followed by HS-A, D were most antileukemically effective ex vivo compared to whole blood control (data not shown). In addition to the results listed, we also compared the antileukemic efficacy WB—in comparison to kit-stimulated WB samples or also to unstimulated T cells. These studies have also shown that not all kits are able to provide comparable and patientindividually variable and antileukemically (more) effective T-cells, so that, in principle, detailed functional analyzes are needed compared to different controls in order to find the patientindividual-best kit which provides the best antileukemic T cell function.

T cells (functional profiles) as well as cytokine profiles before and after stimulation of T cells with whole blood samples (with or without kit treatment) are investigated comparatively to determine whether regulatory or antileukemic, effective T cells as well as memory cells or inhibitory/activating cytokine profiles are generated. For this purpose, flow cytometric analyzes for the determination of cellular profiles as well as analyzes for the determination of cytokine profiles as well as functional analyzes are carried out.

Thus, the presented results suggest that the immunomodulation of blasts with the tested substance mixtures is basically possible and can be achieved on a regular basis, although patient-specific differences occur. These kits can modulate AML blast-containing WB samples, resulting in a good antileukemic efficacy of the T cells stimulated therewith, although this does not work equally well for each kit or individual patient sample. Ultimately, however, the best combination of kits in WB can be determined and ultimately optimized to select the patient's individual best kit for an in vivo application.

Kit Selection:

Table 3 shows the kits prepared according to the invention as well as the most important findings and clinical considerations before use in the patient (details below): The patient-individual best from the first 4 primarily selected kits (HSD, I, K, M) is to be determined and finally administered to the patient. HS-C, F and A are first presented as subordinate kits. The reason for this is that CALCIMYCIN has not yet been used as well as TNFα can no longer be used systemically and TNFα is to be administered in a triple combination. The combination HS-E as well as the single substances HS-G, H and L were tested, are basically possible for use on the patient, but not as efficient in the provision of DC (subtypes) compared to the other combination preparations; HS-E, G, H and L are therefore also subordinated. The preferred kit selection according to the invention shown here is therefore: HS-D, HS-I, HS-K, HS-M. Conceptually, the selection of these kits means that they should develop different immunomodulatory/stimulatory effects (Table 1, 2): in all combination kits GM-CSF is contained, a cytokine that induces and stimulates myeloid cell proliferation and differentiation, the provision and regeneration of stem cells, immunocompetent cells, granulocytes and also of DC generally works without promoting blast proliferation (Table 3).

In the case of kit HS-I (GM-CSF and PICIBANIL), the additional application of the streptococcal lysate is intended to activate immunoreactive cells and the conversion of the myeloid blasts to DCleu, as is already known for the ex vivo generation of DC. Possibly AML patients treated in this way could also benefit from the influence of PICIBANIL on the vascular system (antiangiogenetic effect, increased permeability of the endothelium for immunoreactive cells or humoral factors).

In the case of HS-M (GM-CSF and PGE1), PGE1 is to be administered in addition to GM-CSF. In analogy to PGE2, it was shown that PGE1 also promotes the differentiation of DC; PGE1 is also used (in higher concentrations) for the treatment of VOD disease of patients after SCT. Thus, HS-M might provide a desired additional vasodilatory effect for patients after SCT.

HS-K (GM-CSF and PGE2) and HS-D (GM-CSF and PGE2 and PICIBANIL) are kits containing PGE2. PGE2 increases the maturity or the ability to migrate. HS-D also contains PICIBANIL, possibly enhancing the immunomodulating function of the kit (followed by improved T cell activity).

Subordinate kits: TNFα-containing kits HS-A (GM-CSF and TNFα) as well as HS-C (GM-CSF and TNFα and PGE2) contain TNFα in two- or triple combinations: TNFα is involved as an acute phase protein in inflammatory processes, as a regulator cytokine of cellular processes as well as for activating the immune system—for example, as an inductor of DC maturation. TNFα has so far been used locally for the treatment of soft tissue tumors (in high concentration) and systemically (low concentration) for the treatment of patients with advanced neoplasia. Initially HS-A and HS-C should be used in leukemia patients (in low doses of TNFα) as soon as experience with the first-mentioned kits in the treatment of patients are available. HS-F (GM-CSF and CALCIMYCIN) are also mentioned: CALCIMYCIN has antibiotic action as well as effect on the calcium ion exchange, acts as a decoupler and ATPase inhibitor. In the animal experiment, it has been shown that (i.v. administered) it triggers (in extremely high dosage) inflammations or anaphylaxis. CALCIMYCIN has been used extracorporally to fertilize oocytes in man, but has not yet been applied systematically to humans. It is planned to use HS-F in leukemia patients (in low CALCIMYCIN doses), as soon as experiences with the first-mentioned kits in the patient treatment are available. In the case of kit HS-E (GM-CSF and INTRON) additional activation of the cytokine IFNα2b (=INTRON) could lead to an activation of the immune system as well as to the conversion of the myeloid blasts to DCleu as is known from chronic myelogenous leukemia; HS-E (GM-CSF), HS-H (IFNα2b) and HS-L (PICIBANIL) were basically possible for use on the patient but were shown less efficient in comparison to the combination preparations in providing DC (subtypes); HS-E, G, H and L are therefore to be subordinated.

In the last step, CORRELATION ANALYSIS must be performed to investigate the role or amount of subpopulations of DC, T cells and cytokine concentrations in the context of the antileukemic lytic function. The data are not yet available for evaluation.

Conclusions and Implementation of the Invention in the Clinic:

Even in successfully chemotherapy or stem cell transplanted AML patients often relapse because leukemic cells remain in the body and are ultimately responsible for the relapse. The present invention addresses these residual blasts: they are to be modulated to DCleu with the aid of individually selected and applied kits (consisting of clinically approved substances, growth factors and immune modulators) in such a way that, as a leukemia-antigen presenting 'DC vaccine' activate antileukemic T cells, create an immunological T-cell memory, additionally help to overcome other cellular and humoral immunological barriers and thus protect the patients from relapses.

It could be principally demonstrated that DC/DCleu can be generated from WHOLE BLOOD (WB) of patients with myeloid leukemia (AML) using "standard procedures" as well as minimalized combinations of immunomodulators (kits) and that antileukemic T cells after stimulation arise without inducing blast proliferation. Patient-specific differences were observed: not every kit was successful in every patient, and the antileukemic T-cell activation was not successful in every patient. Thus, in a clinical context, it should be possible-after pre-testing in WB samples- and application of (optimally selected) optimal combinations of immunomodulators to induce the in vivo production of 'DC/DCleu', inducing in vivo antileukemic T cells and thus allow the maintenance of remissions. This TESTING should be performed in cell culture with blast-rich WB samples (taken in acute, blast-rich disease stages), the TREATMENT of the patients should be done in stages, in which the patients are not too much (e.g. disease- or chemotherapy-induced) immunocompromised, to enable a regeneration of immune-competent cells. The present invention is potentially useful for the treatment of all patients of all ages with myeloid leukemia (chronic or acute myelogenous leukemia or myelodysplasia) before or after SCT. The approach is not HLA-restricted and possible without knowledge of leukemic antigens involved. In principle, patients in acute as well as in chronic disease stages/remissions can be treated with the presented concept. The clinical efficacy, tolerability and safety of the individually selected (very low-dose) kits is to be tested in about 10-15 patients at relapse after SCT.

Ex vivo, we have shown that different kits have different effects on individual patient samples or are differently efficient, so that a personalized treatment protocol is to be derived. In every given patient—initially with AML at relapse—the following kits are to be tested on WB samples (HS-I, K, M and possibly D) and the most efficient kit ex vivo for each patient should be selected: a kit that achieves the best blast modulation (Best DC/DCleu subtypes) without inducing a blast proliferation, that induces the most effective antileukemic T-cell response with patient T cells (without causing overshooting T cell responses, e.g., in GvH) and produces the best micromilieu/cytokine profile. By treating the patient with this kit, an overcoming of immunological barriers could be achieved and a functioning cellular and humoral immunity in the patient could be restored.

Primarily, 3-4 kits are to be used in selected relapsed patients after SCT, whose individual substances are well tolerated or even minimize clinically/therapeutically known complications in the mentioned patient group.

In principle, kits with potentially risky components (e.g. TNFα or CALCIMYCIN) could also be used, although severe side effects are not to be expected because of the very low dosage. In principle, the application of single substances (GM-CSF, INTRON, PICIBANIL) would also be possible, but possibly not so effectively in the provision of antileukemic T cells.

The application form (intramuscular (i.m.), subcutaneous (s.c.), intravenous (i.v.), intradermal (i.d.)) is to be carried out according to instructions and recommendations of the pharmaceutical manufacturer (Table 3, column 4). I.v. applications are generally preferred (if possible) in order to ensure as direct a direct influence of the substances on leukemic cells in the blood.

In some cell culture preliminary experiments, it was shown that the sequential (compared to the simultaneous addition) of the substances to the WB cultures gave rise to comparable amounts of DC subtypes (data not shown). It must also be clarified whether GM-CSF i.v. should be administered as a permanent infusion or in frequencies as recommended by the manufacturer.

The duration of the application to the patient can last from at least 3 months to 2 years and must also be decided in the context of clinical application to the patient: The manufacturers of the substances listed here recommend a treatment period of up to 180 days (Table 3, column 7). It is expected that the application will be limited to 3 to 4 months if patients are treated for relapse after SCT. The advantage of using the kits in this patient group is that the effects on (numerous blood) blasts can be directly examined. If these treatments were to accompany DLI treatments, a further advantage would be the administration of defined amounts of T cells, and thus the mainly addressed effector cells. Treatment of patients in remission of the disease in the course of a preservation therapy should be carried out over a period of up to 2 years (in analogy to other maintenance therapies). Depending on the results of a monitoring (see above), an extension or shortening of the recommended treatment time could result.

The dosage of the substances is to be carried out with very low, immunomodulating doses and is based on the concentrations used in the WB cultures; it could in principle also be increased to higher doses as recommended by the manufacturer (Table 3, columns 4 and 5). Probably the optimal dosage will have to be worked out after preliminary experiments in the animal model: First, the selected kits are to be administered in some animal preliminary tests to immunocompromised rats or mice (e.g. NOD-SCID) (to which human AML blasts and T cells were administered): The 2-3 best kits have to be tested in different dosages in parallel (compared to blood samples without kit treatment) in 2-3 immunocompromised mice/rat groups in order to clarify whether there is a blast reduction, an antileukemic T cell activation, T cell subtypes (e.g. effector cells, memory cells) are provided and an activating cytokine milieu is installed.

Table 3 shows the kits according to the invention presented here and gives an overview of their composition, the concentrations of individual substances used ex vivo, as well as clinically relevant considerations on the dosage, application form and duration of the treatment with these. The primary selection of kits according to the invention is: HS-D, HS-M, HS-K, and HS-I. Moreover some data of the DC generation efficiency and antileukemic activity of kit-treated T cells are presented. Here, too, it can be seen that the above mentioned kits show good DC generation or antileukemic activity of stimulated T cells.

Overall, it should be mentioned that no specific treatment protocol for patients is available at the moment. Therefore, dosages, application suggestions, etc. indicated in the text or in the illustrations are intended only as a guide.

Besides examinations of the WB samples before/after their ex vivo processing, regular studies of blood samples of the patients have to be carried out during the in vivo kit treatment (monitoring) in order to record their efficacy and side effects profiles. These examinations must be carried out BEFORE beginning the application (control values) as well as at several points in the course of the treatment. These times should be based on the time points recommended for other immunotherapeutic treatments: First, the quantification of leukemic cells by means of flow cytometry (blast profile) and molecular profiles (overexpression of leukemia-associated antigens, PCR); possibly also DC/DCleu, if they are detectable in the blood. In addition, a characterization of the role involved in the leukemia defense of cellular and soluble factors has to be performed: T cell subpopulations (regulatory, CD4/CD8, memory/effector T cells, T cells with defined Vβ profile, functional characteristics of involved T cells (antileukemic activity) possibly detection of LAA-specific T-cells (Tetramer-analyses), humoral factors (inhibitory (e.g. IL-10, TGFβ, CXCR4)/stimulatory soluble factors, chemokines, cytokines (e.g., IL-2, IL-12, IL-17, IFNγ) measured in cytokine detection assays).

By monitoring of soluble and cellular factors at different timepoints in the course of the disease and by correlating the data with clinical events (for example, relapse), the clinical relevance, treatment success and the prognostic value of our approach can be developed.

It is within the scope of the present disclosure that comments on the various aspects of the invention, as set forth in the appended independent claims, as specifically set forth in connection with one aspect, and also provide an explanation of all other aspects of the invention. To this extent, embodiments of an aspect of the invention are also embodiments of the other aspects of the invention.

Test results from the use of kits in rats with leukemia: In the meantime, the kits were tested in a leukemia rat model, which should also be shown in vivo as an example of the effectiveness of kits: BN—(brown norway) rats as well as PVG.1N rats are rats with the same MHC profile. In BN rats an AML-M3 can be induced by injection of BNML leukemic cells. The leukemia manifests itself within 14-17 days in the spleen, later also in the peripheral blood and then leads to death within 7 days. Blood samples can be taken from the tail vein for cell analyses. After the sacrificing of the animals (after 23 days, shortly before their AML-related death), cell analyses can also be carried out on spleen and blood cells after heart punctions.

Ex Vivo DC/DCleu Generating from WB of Leukemically Diseased Rat:

In analogy to human blast-containing blood, we performed cultivation of AML rat WB with kits HS-D, I, K, M as compared to WB controls. (The same substances as in humans were used, except for rat GM-CSF). First evaluations showed that DCleu can be generated from rat blood from 5 animals as well as from human leukemic WB (on average 10-35% within the entire cell fraction with a convertibility of the blasts to DCleu of 30-50%). The most successful kit was HS-I, followed by HS-M and HS-K. An induction of blast proliferation (co-expression of Ki67) was seen after treatment with none of the kits. In addition, after co-culture of DCleu-containing kit-treated WB samples with autologous rat T cells, increased blast lytic activity against BNML blasts could be detected in all kits. The highest antileukemic activity had HS-I-WB-stimulated T cells. More detailed analyzes are still pending. Since basically blasts in rat blood were convertible to DCleu now in vivo treatments should be carried out.

In Vivo Treatment of PVG.1N Rats with Picibanil, PGE1 and PGE2 (Safety Data):

Safety data were performed on a total of 4 rats of the healthy strain PVG.1N: they were given the clinically intended final concentrations of the single substances i.v. in the following doses: Picibanil (0.35 µg/rat), PGE2 (1 µg/rat), PGE1 (1 µg/rat) and placebo (PBS). The rats showed no (severe) side effects (S) AE: breathing, sleep, food intake, mobility, skin, weight were completely normal or as in control animals (data not shown). Flow cytometric analyzes on blood cells of the PVG.1N rats showed no difference compared to the placebo controls (Teff, Treg, CD4, CD8, NK, NKT cells, data not shown).

In Vivo Treatment of Leukemic Diseases BN Rats with Kits (Efficacy Data):

Since the tolerability of the substances we use is very good, now BN rats were treated after induction of leukemia (day 0) on days 14 and 17 with 4 kits compared to the placebo controls (i.v. administration in penile vein, see FIG. 5A: 3 rats each received:

HS-$I_{low}$: GM-CSF (1 µg/rat)+Picibanil (0.175 µg/rat, corresponding to 0.5 KE in humans)

HS-$I_{high}$: GM-CSF (1 µg/rat)+Picibanil (0.35 µg/rat, corresponding to 1 KE in humans)

HS-K: GM-CSF (1 µg/rat)+PGE2 (1 µg/rat)

HS-M: GM-CSF (1 µg/rat)+PGE1 (1 µg/rat)

Placebo: PBS

The efficacy of the kits was determined on day 23 as a comparison of the blast proportions in blood and spleen after kit treatment compared to placebo control: While HS-$I_{low}$ (with low-dose Picibanil) and HS-K (PGE2-containing) did not show differences in blast proportions compared to controls the blast portions after treatment with HS-$I_{high}$, were reduced by 4.4-6.3% in blood or spleen, after HS-M treatment the blast portions were even significantly reduced by 10.7-15.8%.

Analysis of the immunoreactive cells in the blood at the time of the sacrifice of the rats revealed the following picture: CD62L+CD4+bw CD8+ T(memory) cells were increased by 10.4% (CD4+) or 21.1% (CD8+) in rats' blood (FIG. 5C). The percentage reduction of CD4+FoxP3+ CD25+ regulatory Tcells after treatment of the rats with all kits (by −24.3% (HS-$I_{low}$) to −55.6% (HS-M)) in the spleen was also noticeable in comparison to control (FIG. 5D). Further data on immunoreactive cells are not yet available.

In summary, our results obtained with rat blood show that the ex vivo generation of DC/DCleu is similar to that achieved with human WB without increasing the proliferation of the blasts. The treatment of healthy rats with the single substances showed a very good compatibility of the substances; The treatment of AML-M3 leukemia-mediated BN rats with different kits HS-K, M, I showed that a blast reduction of up to 15.8% could be achieved in only 10 days of treatment with our immunomodulatory treatment concept Well in this leukemia form, but not every kit works equally well in this leukemia form.

CONCLUSIONS

Based on the present invention, it will be possible at an early stage to develop an "in vivo protocol" which allows the application of minimalized combinations of immunomodulators (without need for a GMP facility) for patients with myeloid leukemia. The detailed design of a personalized treatment protocol for patients with myeloid leukemias with different or differently combined immunomodulatory single substances as well as the detailed concept of an immune monitoring must be carried out after consultation with treating physicians before the start of the treatments and will be based on other immunotherapeutic treatment protocols. Expertise in immunotherapeutic treatments is given to the institutions for the treatment of patients. A routinely collected diagnostic support program for the examination of the blood samples as well as clinical findings on patient profiles is available.

Thus, experience, expertise, and synergisms available for the clinical implementation of the invention can be used to treat-initially-AML patients at relapse after allogeneic SCT.

TABLE 1

Generation of DC/DCleu from AML-blast-containing Mononuclear cells (MNC) or Whole Blood (WB)-cells with various DC-differentiation methods or specific kits a) DC-differentiation methods or specific kits for the generation of DC/DCleu from blast-containing MNC (a1-a4) or WB (a1-a5)

|  | 'CA' a.1 | 'MCM' a.2 | 'PICI' a.3 | 'INTR' a.4 | 'Kits': HS-A, C, D, E, F, G, H, I, K, L, M* a.5 |
|---|---|---|---|---|---|
| DC-generating methods |  |  |  |  |  |
| Culture time [d] | 3-4 days | 10-14 days | 9-11 days | 10-14 days | 8-10 days |
| DC-generating methods | IL-4, CALCIMYCIN | GM-CSF, IL-4, TNFα, IL-1β, IL-6, PGE$_2$, | GM-CSF, TNFα, PGE$_2$, PICIBANIL | GM-CSF, INTRON, TNFα | Various combinations of 1-3 clinically approved single substances/immune modulators |

TABLE 1-continued

Generation of DC/DCleu from AML-blast-containing Mononuclear cells (MNC) or Whole Blood (WB)-cells with various DC-differentiation methods or specific kits

| Mechanism of Action | Bypass of the cytokine induced DC differentiation | Cytokine-induced DC-differentiation; PGE$_2$ increases CCR7-expression and improves migration | Bacterial lysate and PGE$_2$ stimulate DC-differentiation | Cytokine-induced DC-differentiation | DC differentiation by combination of immune modulators/danger-factors/cytokines |
|---|---|---|---|---|---| b): Advantages and value of DC generation from whole blood samples

| Advantages | Comments on the clinical relevance or implementation in a clinical application |
|---|---|
| Simulation of a physiological system | Transferability to the clinic |
| Capability to quantify and qualitatively characterize cells involved in responses | Conclusions on biological mechanisms/reaction profiles |
| Proportions of blasts | possible increase in blasts can be quantified |
| T cell (sub)populations, NK, NKTcells | interesting immunereactive cells (e.g.: regulatory, effectormemory, integrin-positive Tcells, NK, NKT-cells |
| Success of a blast conversion to DCleu or DCsubtypes well quantifiable | In vivo, DC in the blood are difficult to quantify because of their migration into the tissue |
| Analysis of the microenvironment on immunostimulating and -inhibiting influences possible | Detection of, escape'- or antileukemic mechanisms and possible interactions; Development of appropriate therapeutic strategies |
| Functional tests possible in whole blood | Antileukemic responses quantifiable (decrease/increase of blasts), effector cell profiles measurable (proliferation, subtypes) |

PGE$_2$: Prostaglandin E2;
IL-4,-1β,-6: interleukin 4, -1β, -6;
PICIBANIL: OK432 (Bacterial lysate from *stretococcus pyogenes*);
INTRON: Interferon alpha 2b;
FL FLT3 Ligand TNFα: tumor necrosis factor alpha;
GM-CSF: granulocyte macrophage colony stimulating factor;
*Details see Table 2

TABLE 2

Active ingredients in the kits for the immunomodulation of AML blasts

| Active substance | Functions/effects | Previous clinical applications |
|---|---|---|
| GM-CSF Leukine Sargramostin) | induces proliferation and differentiation of hematopoietic cells (precursor cells, neutrophils, monocytes, macrophages, myeloid DC) reduces duration of neutropenia reduces incidence of infections reduces administrations of antimicrobial substances | (1) AML patients >55 years: after chemotherapy to reduce neutrophil recovery, to reduce the incidence of infections (2) mobilization of stem cells into the PB (for the collection of stem cells) (3) Myeloid cell reconstitution after autologous/allogenic SCT of ALL, NHL, HD (4) Treatment of transplant failure after autologous/allogeneic SCT (5) Monocyte/DC activation in melanoma patients in vivo (6) Immune modulation of blasts (s.c or iv) |
| TNFα Kachexin | Cytokine, which activates acute phase proteins Induction of apoptosis, cell proliferation, differentiation, cytokine release triggering of inflammation, necrosis, cachexia, fever Autoimmune-reactions, | (1) Local treatment of sarcoma, non-resectable tumors, melanomas of the extremities (2) Systemic (i.v.) treatment of patients with advanced neoplasia |
| INTRON IFNα2b | Cytokine with immunomodulating effect important in the defense of virus infected cells, important in the | (1) Treatment of hepatitis B and C (2) Treatment of CML (3) treatment of myelomas, (4) Treatment of follicular lymphomas (5) Treatment of carcinoid tumors |

TABLE 2-continued

Active ingredients in the kits for the immunomodulation of AML blasts

| Active substance | Functions/effects | Previous clinical applications |
|---|---|---|
| | activation of the immune system<br>regulators of cell proliferation | (6) treatment of melanomas,<br>(7) Treatment of hairy cell leukemia<br>(Administration i.v, i.m., s.c.: in healthy volunteers i.v and s.c/i.m. applications comparable) |
| $PGE_1$ (Alprostadil) | vasodilatorial properties (increase in blood flow) anti platelet activity | (1) Treatment of Venoocclusive Disease (VOD) after SCT<br>(2) treatment of erectile dysfunction<br>(3) Preservation of the Ductus Arteriosus Botalli<br>(4) Treatment of ischemia of the extremities (I.v administration) |
| $PGE_2$ (ProstinE2) | is formed by (activated) blood platelets, possibly produced by erythrocytes (by activation of Ca transport in Erys): involved in coagulation! contracting | (1 induction of labour, birth promotion, introduction of abortion<br>(2) Application iv, sc, im |
| PICIBANIL OK432 (Chugai Pharma) | *Streptococcus pyogenes* (low virulent, H2O2 and penicillin-treated) induces activation of immunoreactive cells, cytokine release, increases permeability of endothelium, antiangiogenetic effect (Hitayama 2013) | (1) intralasional treatment of benign lymphatic tumors (lymphangiomas, cystic hygromae), head and neck tumors<br>(2) intrauterine treatment of cystic hygroma<br>(3) Intratumoral injection of immature DC and OK432 in or near tumors of pancreas carcinoma<br>(4) Induction of pleurodesis by pleural infusion of OK432<br>(5) Immunomodulation in squamous cell carcinomas (Id or near the tumor)<br>I.m., i.d or s.c according to approval |
| CALCIMYCIN, CalciumIonophor, A23187 (Sigma) Product of *Streptomyces chartreusensis* | Antibiotic activity against gram-positive bacteria increases intracellular Ca + 2 ion concentrations decoupler of oxidative phosphorylation inhibitor of mitochondrial ATPase | (1) Ex vivo: Treatment of oocytes before in vitro fertilization<br>(2) Pig: i.v. administration (high dose 5 mg/kg) indicates anaphylactic shock<br>(3) Rat: intrapleural injection produces pleurisy<br>(4) Guinea pigs: Inhalation produces pneumonia |

TABLE 3

Composition of the tested kits

Comments on 1, 2, 3,

Clinical considerations:
PLANNED in vivo method of administration (AA), dosage (Do): indicated as range ($Do^R$) as well as in a immunemodulatory context/related to 6 L blood ($Do^I$), frequency of administration (VF) and -duration (VD)

| Kits | in CELL CULTURE | AA (bold: Planned) | $Do^R$<br>(1) µg/m²<br>(2) mio I.E/m²<br>(3) µg/day<br>(4) mg/kg/day<br>(5) µg/m²/day<br>(6) µg/week (=we)<br>(7) mg/m²/day | $Do^I/[6I]$ | VF | VD (overall: 3 months up to 2 years) | (1)Efficiency of DC- generation N/NN (%) | (2)anti- leukemic T-cell- function N/NN (%) |
|---|---|---|---|---|---|---|---|---|
| HS-D: | | | | | | | | |
| GM-CSF | 800 U/ml, | ic/sc/iv | 15-500 (1) | 75(5) | ca3-7x/we | 7-42 days | 38/43 (88%) | 10/14 (71) |
| PICIBANIL | 10 µg/ml, | im, sc, id | 20-500(3) | 50(6) | ca3-7x/we | −21 days | | |
| $PGE_2$ | 1 µg/ml, | iv, sc, im | 0.1-5 (4) | | ca3-7x/we | 7-42 days? | | |
| HS-E: | | | | | | | | |
| GM-CSF | 800 U/ml, | ic/sc/iv | 15-500 (1) | 75(5) | ca3-7x/we | 7-42 days | 15/25 (60%) | 6/9 (67) |
| INTRON | 500 U/ml | iv/sc/im | 2-5 (2) | 3-3.5 mio | ca 3-7x/we | −180 days | | |
| HS-I: | | | | | | | | |
| GM-CSF | 800 U/ml, | ic/sc/iv | 15-500 (1) | 75(5) | ca3-7x/we | 7-42 days | 30/30 (100%) | 14/19 (74) |
| PICIBANIL | 10 µg/ml | im, sc, id | 20-500(3) | 50(6) | ca3-7x/we | −21 days | | |

TABLE 3-continued

Composition of the tested kits

Comments on 1, 2, 3,

Clinical considerations:
PLANNED in vivo method of administration (AA), dosage
(Do): indicated as range ($Do^R$)
as well as in a immunemodulatory context/related to 6 L blood
($Do^I$), frequency of administration (VF) and -duration (VD)

| Kits | in CELL CULTURE | AA (bold: Planned) | $Do^R$<br>(1) µg/m²<br>(2) mio I.E/m²<br>(3) µg/day<br>(4) mg/kg/day<br>(5) µg/m²/day<br>(6) µg/week (=we)<br>(7) mg/m²/day | $Do^I$/[6I]<br>VF | VD (overall: 3 months up to 2 years) | (1)Efficiency of DC-generation N/NN (%) | (2)anti-leukemic T-cell-function N/NN (%) |
|---|---|---|---|---|---|---|---|
| HS-K: | | | | | | | |
| GM-CSF | 800 U/ml, | ic/sc/iv | 15-500 (1) | 75(5) | ca3-7x/we | 7-42 days | 13/13 (100%) | 7/9 (78) |
| PGE₂ | 1 µg/ml, | iv, sc, im | 0.1-5 (4) | | ca3-7x/we | 7-42 days? | | |
| HS-M: | | | | | | | |
| GM-CSF | 800 U/ml, | ic/sc/iv | 15-500 (1) | 75(5) | ca3-7x/we | 7-42 days | 3/4 (75%) | 3/3 (100) |
| PGE₁ | 1 µg/ml, | iv | 0.075-500(3) | | ca7x/we | –30 days | | |
| HS-A: | | | | | | | |
| GM-CSF | 800 U/ml, | ic/sc/iv | 15-500 (1) | 75(5) | ca3-7x/we | 7-42 days | 36/44 (82%) | 3/3 (100) |
| TNFα | 10 ng/ml | iv | 0.04-4 (7) | | | | | |
| HS-C: | | | | | | | |
| GM-CSF | 800 U/ml, | ic/sc/iv | 15-500 (1) | 75(5) | ca3-7x/we | 7-42 days | 30/37 (81%) | 5/9 (56) |
| TNFα | 10 ng/ml, | iv | 0.04-4 (7) | | ca3-7x/we | | | |
| PGE₂ | 1 µg/ml, | iv, sc, im | 0.1-5 (4) | | ? | 7-42 days? | | |
| HS-F: | | | | | | | |
| GM-CSF | 800 U/ml, | ic/sc/iv | 15-500 (1) | 75(5) | ca3-7x/we | 7-42 days | 42/45 (93%) | 11/14 (79) |
| CALCIMYCIN | 375 ng/ml | ex vivo | 5-10 µM | | once | once | | |
| HS-G: | | | | | | | |
| GM-CSF | 800 U | ic/sc/iv | 15-500 (1) | 75(5) | ca3-7x/we | 7-42 days | 18/27 (66%) | |
| HS-H: | | | | | | | |
| INTRON | 500 U/ml | iv/sc/im | 2-5 (2) | 3-3.5 mio | ca 3-7x/we | –180 days | 4/12 (33%) | |
| HS-L: | | | | | | | |
| PICIBANIL | 10 µg/ml | im, sc, id | 20-500(3) | 50(6) | ca3-7x/we | –21 days | 6/9 (67%) | 16/22 (73) |
| w/o | | | | | | | 6/41 (15%) | |

\* Based on 6 liters of blood, according to the drug concentrations used in vitro W/o WB control without kits

The invention claimed is:

1. A method of treating a subject suffering from acute myeloid leukemia (AML) or myelodysplastic syndromes (MDS), comprising: administering to a subject an effective amount of a composition comprising Granulocyte-Macrophage Colony-Stimulating Factor (GM-CSF) and at least one agent, wherein the at least one agent comprises Prostaglandin E1 (PGE1) or Picibanil.

2. The method of claim 1, wherein the at least one agent is PGE1.

3. The method of claim 1, wherein the at least one agent is Picibanil.

4. The method of claim 1, wherein the composition further comprises a pharmaceutically acceptable binder.

5. The method of claim 1, wherein the composition is administered parenterally.

6. The method of claim 1, wherein the subject is an immunocompetent human.

7. The method of claim 1, wherein the GM-CSF is administered to the subject at selected dosage times over a selected dosage period; and a first agent of the at least one agent is administered to the subject at dosage times that alternate with the dosage times of the GM-CSF over the dosage period.

8. The method of claim 1, wherein the at least one agent is Picibanil, and wherein the administration to the subject comprises:
   administering GM-CSF as an intravenous continuous infusion or intramuscularly, intradermally or subcutaneously with a dose of from about 15 µg/day up to about 500 µg/day; and
   administering Picibanil as an intravenous continuous infusion or intramuscularly, intradermally or subcutaneously with a dose of from about 20 µg/day up to about 500 µg/day;
   wherein the doses of GM-CSF and Picibanil are administered in this order in a daily, two-day or three-day interval.

9. The method of claim 1, wherein the at least one agent is PGE1, and wherein the administration to the subject comprises:
   administering GM-CSF as an intravenous infusion with a dose of from about 15 µg/m²/day up to about 500 µg/m²/day; and administering PGE1 as an intravenous infusion with a dose of from about 0.075 µg/kg/day up to about 500 µg/kg/day; in daily, two-day or three-day intervals, wherein GM-CSF is administered prior to PGE1.

10. A method of reducing relapse or progression of acute myeloid leukemia (AML) or myelodysplastic syndromes (MDS) in a subject, comprising administering to a subject an effective amount of a composition comprising Granulocyte-Macrophage Colony-Stimulating Factor (GM-CSF) and at least one agent, wherein the at least one agent comprises Prostaglandin E1 (PGE1) or Picibanil.

* * * * *